United States Patent
Borden et al.

(10) Patent No.: US 9,107,950 B2
(45) Date of Patent: Aug. 18, 2015

(54) SYSTEMS, METHODS, AND DEVICES FOR MICROBUBBLES

(75) Inventors: Mark A. Borden, Boulder, CO (US); Edward J. Swanson, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 13/394,162

(22) PCT Filed: Sep. 15, 2010

(86) PCT No.: PCT/US2010/048887
§ 371 (c)(1),
(2), (4) Date: Apr. 24, 2012

(87) PCT Pub. No.: WO2011/034892
PCT Pub. Date: Mar. 24, 2011

(65) Prior Publication Data
US 2012/0201900 A1     Aug. 9, 2012

Related U.S. Application Data

(60) Provisional application No. 61/242,768, filed on Sep. 15, 2009.

(51) Int. Cl.
| | |
|---|---|
| A61K 9/16 | (2006.01) |
| A61K 9/127 | (2006.01) |
| F17B 1/00 | (2006.01) |
| B01F 3/02 | (2006.01) |
| F26B 5/06 | (2006.01) |
| A61K 49/22 | (2006.01) |
| B01J 13/04 | (2006.01) |
| B01J 13/02 | (2006.01) |
| A61K 9/00 | (2006.01) |

(52) U.S. Cl.
CPC ............... *A61K 49/223* (2013.01); *B01J 13/04* (2013.01); *A61K 9/0026* (2013.01); *B01J 13/02* (2013.01)

(58) Field of Classification Search
None
See application file for complete search history.

(56) References Cited

U.S. PATENT DOCUMENTS

| | | | | |
|---|---|---|---|---|
| 3,724,673 | A * | 4/1973 | Ryon | ........................ 210/500.27 |
| 5,380,519 | A | 1/1995 | Schneider et al. | |
| 5,531,980 | A | 7/1996 | Schneider et al. | |
| 5,567,414 | A | 10/1996 | Schneider et al. | |
| 5,626,833 | A | 5/1997 | Schutt et al. | |
| 5,643,553 | A | 7/1997 | Schneider et al. | |
| 5,658,551 | A | 8/1997 | Schneider et al. | |
| 5,665,383 | A | 9/1997 | Grinstaff et al. | |
| 5,911,972 | A | 6/1999 | Schneider et al. | |
| 6,110,443 | A * | 8/2000 | Schneider et al. | ........... 424/9.51 |
| 6,136,293 | A | 10/2000 | Schneider et al. | |
| 6,217,850 | B1 | 4/2001 | Dugstad et al. | |
| 6,649,145 | B2 | 11/2003 | McGrath et al. | |
| 7,109,167 | B2 | 9/2006 | Von Wronski et al. | |
| 2001/0010811 | A1 * | 8/2001 | Dugstad et al. | ............... 424/9.52 |
| 2004/0180004 | A1 | 9/2004 | Schneider et al. | |
| 2007/0059248 | A1 * | 3/2007 | Unger et al. | ................. 424/9.52 |
| 2007/0071685 | A1 | 3/2007 | Schneider et al. | |
| 2007/0128117 | A1 | 6/2007 | Bettinger et al. | |

FOREIGN PATENT DOCUMENTS

| | | | |
|---|---|---|---|
| WO | 94/28780 | A2 | 12/1994 |
| WO | 97/00638 | | 1/1997 |
| WO | 97/40858 | A1 | 11/1997 |
| WO | WO 9740858 | A1 * | 11/1997 |
| WO | 98/18501 | | 5/1998 |
| WO | 2009/043031 | | 4/2009 |
| ZA | 9807483 | A | 5/1999 |
| ZA | 9807483 | A * | 7/1999 |

OTHER PUBLICATIONS

Bisazza et al., "Microbubble-Mediated Oxygen Delivery to Hypoxic Tissues as a New Therapeutic Device," *Conference Proceedings of the Annual International Conference of the IEEE Engineering in Medicine and Biology Society*, 2008, 2008: pp. 2067-2070.

Cho et al., "Dynamic Surface Tension of Stable Air-Filled Microbubbles Prepared by Freeze-Drying a Solution of Lipid/Surfactant Mixture," *Colloids and Surfaces A: Physicochemical and Engineering Aspects*, 2006, 284: pp. 453-457.

Feshitan et al., "Microbubble Size Isolation by Differential Centrifugation," *Journal of Colloid and Interface Science*, Jan. 2009, 329(2): pp. 316-324.

Lundgren et al., "Intravascular Fluorocarbon-Stabilized Microbubbles Protect Against Fatal Anemia in Rats," *Artificial Cells, Blood Substitutes, and Immobilization Biotechnology*, 2006, 34(5): pp. 473-486.

Extended European Search Report, issued Nov. 4, 2013, in European Patent Application No. 10817738.7.

* cited by examiner

*Primary Examiner* — Isaac Shomer
(74) *Attorney, Agent, or Firm* — Miles & Stockbridge P.C.; Mark A. Catan

(57) ABSTRACT

A suspension of gas-filled microbubbles can be synthesized by sonicating a lipid solution and a first gas in a reaction volume. The resulting microbubble suspension can be stored for later use, for example, for infusion into a patient for gas delivery thereto. Various techniques can improve the shelf life of the microbubbles. For example, the microbubble suspension can be freeze-dried to remove water and the first gas therefrom while leaving the microbubble shells intact. In an alternative, the microbubble suspension can be frozen. In still another alternative, the microbubble suspension can be formed with a first gas that has a low solubility, thereby creating microbubbles with increased stability. Prior to use, the microbubble suspension can be prepared by exchanging the gas in the microbubble cores, rehydrating, and/or raising the temperature of the stored microbubbles.

20 Claims, 6 Drawing Sheets

SYSTEMS, METHODS, AND DEVICES FOR MICROBUBBLES

CROSS-REFERENCE TO RELATED APPLICATIONS

The present application is a U.S. national stage of International Application No. PCT/US10/48887, filed Sep. 15, 2010, which claims the benefit of U.S. Provisional Application No. 61/242,768, filed Sep. 15, 2009, both of which are hereby incorporated by reference herein in their entireties.

FIELD

The present disclosure is directed generally to microbubble solutions, and, more particularly, to systems, methods, and devices for production, storage, and/or use of microbubble solutions.

BACKGROUND

Microbubbles have been used, for example, in the field of ultrasound imaging as contrast agents. However, such imaging applications may need relatively few microbubbles, for example, on the order of $10^6$-$10^8$ microbubbles per injection. Such quantities can be achieved using low volume batch production techniques. However, for some medical and industrial applications, greater quantities of microbubbles may be required, for which low volume batch production techniques may be inadequate. In addition, current storage techniques may be inadequate to maintain large quantities of microbubbles for significant periods of time.

SUMMARY

A solution of gas-filled microbubbles can be synthesized by sonicating a lipid solution and a first gas in a reaction volume. The resulting microbubble solution can be stored for later use, for example, for infusion into a patient for gas delivery thereto. In any embodiments, the microbubbles can be freeze-dried to remove water and the first gas therefrom while leaving the microbubble shells intact. In embodiments, this may have the effect of improving the shelf life of the microbubbles. In an alternative embodiment, the microbubbles can be frozen. In still another alternative embodiment, the microbubbles can be formed with a first gas that has a low solubility, thereby creating microbubbles with increased stability. In any of these embodiments, prior to use, the microbubbles can be prepared by exchanging the gas in the microbubble cores, rehydrating, and/or raising the temperature of the stored microbubbles.

In embodiments, a method for generating microbubbles includes flowing a lipid solution and a first gas into a reaction volume. An interface between the lipid solution and the first gas in the reaction volume can be ultrasonically agitated so as to generate a suspension of microbubbles. Each microbubble can have a lipid monolayer shell surrounding a core of the first gas. The method can further include freeze-drying at least a portion of the generated microbubbles such that water and the first gas are removed therefrom. At a later time, the freeze-dried microbubbles can be exposed to an atmosphere composed substantially of a second gas.

In embodiments, a microbubble system can include a microbubble synthesis unit, a freeze-drying unit, a storage unit, and a gas exchange unit. The microbubble synthesis unit can be configured to generate a plurality of microbubbles by ultrasonically agitating an interface between a lipid solution and a first gas in a reaction volume. Each microbubble can have a lipid monolayer shell surrounding a core of the first gas. The freeze-drying unit can be configured to freeze the plurality of microbubbles and to remove water and the first gas therefrom. The storage unit can be configured to package the freeze-dried microbubbles in a sealed environment. The gas exchange unit can be configured to expose microbubbles from the storage unit to an atmosphere of a second gas such that the core of each microbubble is filled with the second gas.

In embodiments, a microbubble infusion device can include a temperature control module and a processing module. A temperature control module can be configured to control a temperature of a population of microbubbles. The processing module can be configured to mix the microbubbles and to remove bubbles having a diameter greater than 10 μm therefrom prior to use, such as infusion into a patient.

Objects and advantages of embodiments of the present disclosure will become apparent from the following description when considered in conjunction with the accompanying drawings.

BRIEF DESCRIPTION OF THE DRAWINGS

Embodiments will hereinafter be described with reference to the accompanying drawings, which have not necessarily been drawn to scale. Where applicable, some features may not be illustrated to assist in the illustration and description of underlying features.

DETAILED DESCRIPTION

Figure 1:
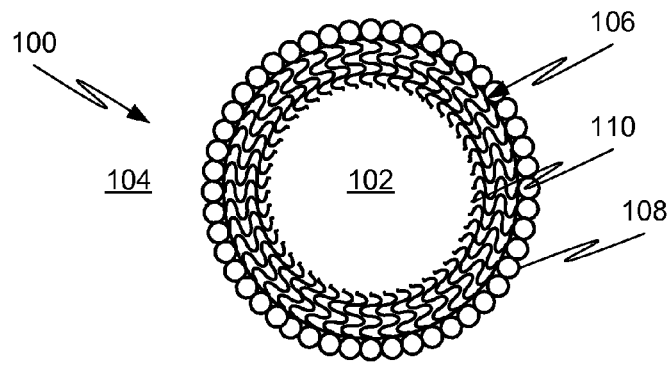
FIG. 1 is a schematic diagram of a gas-filled microbubble, according to one or more embodiments of the disclosed subject matter.

As used herein, microbubbles refer to bubbles on the order micron size. For example, bubbles in the range of 0.5 µm to 10 µm in diameter may be selected for certain applications. Microbubbles are generally substantially-spherical gas-filled particles in solution that are stabilized by an organic coating at the gas-liquid interface. A microbubble 100 is illustrated schematically in FIG. 1. The microbubble 100 has a gas core 102 surrounded by a lipid shell 106 in a generally spherical structure. Each lipid molecule has a hydrophilic head 108 and a hydrophobic tail 110. Intermolecular interactions with the solution 104 surrounding the microbubble 100 cause the lipid molecules to organize at the interface between the gas and the solution to form a monolayer 106 around the gas core 102.

Gas release properties and biocompatibility of the microbubbles can be controlled via the formulation of the shell material (i.e., the microbubble shell). For example, mixtures of a phospholipid, such as dipalmitoylphosphatidylcholine (DPPC) or distearoylphosphatidylcholine (DSPC), and a polyethylene glycol (PEG) chain-based emulsifying agent (e.g., polyethylene glycol 40 stearate (PEG40S)) can be used for the microbubble shell. The phospholipid and the emulsifier may be combined in a molar ratio of, for example, 9:1. Such a shell self-assembles during the fabrication process thereby resulting in a lipid monolayer of approximately 10 nm in thickness. The vast majority of the microbubble volume is thus available for gas storage.

Microbubbles can have a high surface area-to-volume ratio, which makes them ideal vehicles for the rapid delivery of gasses in a variety of applications. Moreover, the relatively small thickness of the shell presents a minor barrier to release of the gas. Because the materials for the microbubble coating are biologically derived, they also do not pose any biocompatibility concerns. The materials for the microbubble shell disclosed herein may be relatively inexpensive; however, other shell materials may also be used to enhance microbubble stability depending on the desired application.

The biocompatibility, gas delivery capability, and size of the microbubbles allow them to be used for gas delivery to a target, such as a patient. For example, by injecting the microbubbles filled with oxygen intravenously, the blood stream of a patient can be oxygenated in a minimally invasive manner. In embodiments, a microbubble system can produce large quantities of microbubbles, for example, a quantity sufficient to meet the respiratory needs of an average human (e.g., 200-250 mL of oxygen per minute). Such microbubbles may be produced from a quantity of stored microbubbles as described herein. Microbubbles can be used to provide gas in any kind of application where rapid dissolution of a gas is required, for example, a fuel cell or chemical production process. In such applications, the shell material can be recovered and recycled through suitable separation techniques.

The concentration of the microbubbles in a suspension (i.e., the percent volume of gas in a suspension) as well as the sizes of the microbubbles can be tailored for a specific application by appropriate control of the fabrication parameters of the microbubble generation system. Production and storage of oxygen microbubbles may be an important technology for a number of applications, including intravenous oxygenation of a patient's bloodstream. For some applications, microbubble size distribution between 0.5 µm and 10 µm in diameter may be usefully employed. A percent volume of gas higher than 50% oxygen by volume may be obtained. Higher gas volume percentages may also be employed (for example, 80-90%) according to one or more contemplated embodiments.

Microbubble embodiments employing phospholipid-emulsifier formulations can be biocompatible, but may have a limited shelf life at room temperature. For example, the microbubbles may be relatively stable at room temperature for about one week, which may limit their utility. When microbubbles are generated off-site and/or are not immediately needed, a longer shelf life may be desirable. For example, the microbubbles can be fabricated at a manufacturing facility and shipped to an end user location, such as hospital, for use in a desired application. In addition, an extended shelf life may also allow stockpiling of microbubbles for emergencies, large volume applications, or other uses. Storage methods, systems, and devices, as described herein can greatly extend the shelf life of lipid shell microbubbles.

In embodiments, the shelf life of microbubbles may be extended by freezing the microbubble suspension. In particular, the microbubble suspension may be frozen at temperatures significantly below the freezing point of water. In an embodiment, the microbubbles are frozen below −20° C. In another embodiment, the microbubbles are frozen using dry ice at a temperature around −78.5° C. In still another embodiment, the microbubbles are frozen using liquid nitrogen.

Figure 2:
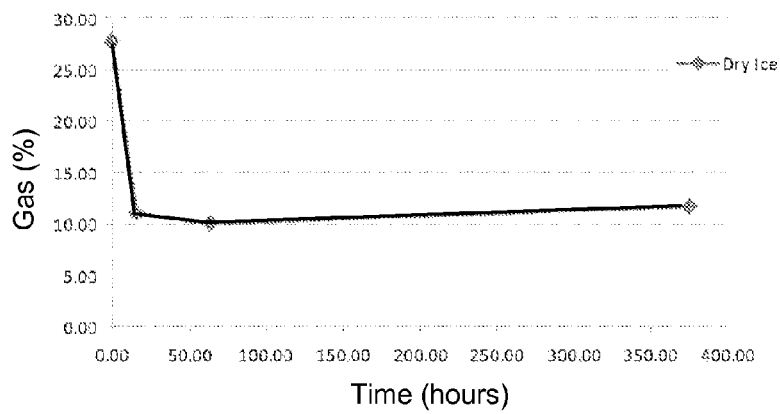
FIG. 2 is a graph of percent gas volume versus time for a microbubble suspension frozen using dry ice.

When frozen, the ability of the microbubbles to retain the gas within the core may be compromised. For example, for microbubbles stored at dry ice temperatures (e.g., around −78.5° C.), the gas percentage in the microbubbles may be reduced once recovered (i.e., thawed). FIG. 2 shows a graph of the gas volume percentage of the microbubbles recovered from the frozen suspension as a function of time stored. The data illustrates that in microbubbles recovered from the frozen suspension, the gas percentage level seems to drop and remain at around 10%—a drop in gas volume percentage of approximately 17%. Moreover, this gas percentage loss does not seem to be affected by the duration of storage.

Figure 3:
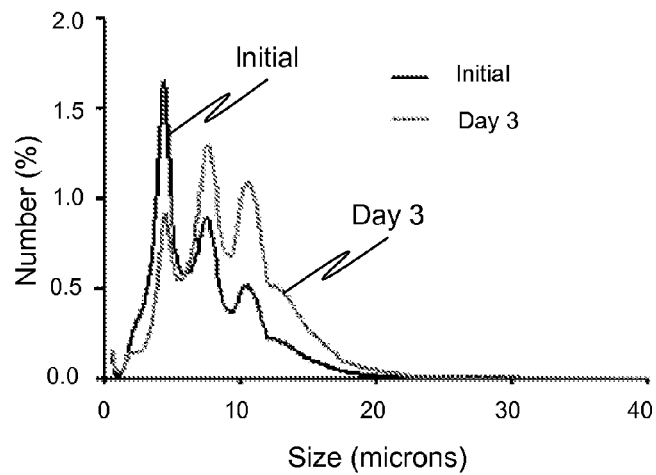
FIG. 3 is a graph of size distribution for a microbubble suspension frozen using dry ice.

FIG. 3 shows the size distribution of the microbubbles recovered from the frozen suspension after three days versus an initial size distribution of the microbubbles. As show, there is only a slight variation in the size distribution after three days of freezing. Based on the two large peaks for sizes less than 10 µm in the figure, most of the frozen microbubbles maintain a size within the range of the initial size distribution. The microbubbles can thus be recovered after freezing and be used for medical purposes.

Because freezing forms ice crystals that can adversely affect the shell integrity and the gas retention ability of the shell, fast freezing rates (e.g., on the order of seconds) can minimize or at least reduce the amount of microbubble loss and/or variation. Frozen microbubbles allowed to thaw at room temperature may also be compromised since slower heating rates may allow crystals formed during freezing to grow. As with freezing, this crystal growth during thawing may adversely affect microbubble integrity. To overcome this problem, rapid melting (e.g., on the order of seconds) may be performed by exposing the frozen microbubbles to high temperatures (e.g. 60° C.) immediately after removing from refrigeration (e.g., dry ice temperatures).

In embodiments, the shelf life of microbubbles may be extended by freeze-drying the microbubbles. In particular, the microbubbles are subjected to a freeze-drying process, or lyophilization, where the bulk of water in the microbubble suspension is removed at low pressure. The gas that was in the core may be removed with the water during the lyophilization process, thereby leaving only dried lipid monolayer shells behind. The dried microbubbles can be stored in an evacuated environment. Alternatively, the dried microbubbles may be stored in a gas environment that does not adversely affect the microbubble shell material, such that any degradation of the phospholipid materials due to chemical reactions, such as a reaction with oxygen, may be reduced or eliminated.

The dried microbubble shell can be stored at room temperature in embodiments. In other embodiments, the dried microbubbles are stored at a reduced temperature (e.g., −78.5° C.) until ready for use. Prior to use, the microbubbles may be backfilled with the desired core gas, which may be the same or different from the gas used to generate the microbubbles. When a highly concentrated suspension of microbubbles is required at a later time, an aqueous solution can be added to re-disperse the gas-filled microbubbles.

When using certain gases, such as oxygen, for the core gas, degradation of the phospholipid may result over time, thereby affecting the stability of the microbubbles. In addition, certain gases, such as oxygen, can have a relatively high solubility in water, which may allow such gases to exit or disrupt the microbubble core prematurely. In embodiments, some egress of gas may be desirable, but solubility effects may require strict management. Other gases that are insoluble or at least have a lower solubility for the microbubble-forming solution can be used to produce more stable microbubbles and to avoid degradation of the lipid shell. For example, a gas such as sulfur hexafluoride ($SF_6$) or a perfluorocarbon (e.g., perfluorobutane) can be used to generate and/or store the microbubbles.

In embodiments, the shelf life of microbubbles may thus be extended by using an insoluble or low solubility gas to form the microbubbles. In particular, the microbubbles are generated with a first gas, which is an insoluble or low solubility gas. The generated microbubbles can then be subjected to a freeze-drying process, or lyophilization, where the bulk of water in the microbubble suspension is removed at low pressure, thereby leaving behind the lipid monolayer shells in the desired size range. The dried microbubbles may be stored in an environment of substantially the first gas or under vacuum until ready for use. Alternatively, the generated microbubbles can be stored in an environment of substantially the first gas without freezing or freeze drying until ready for use. Prior to use, the microbubble core can be filled with the desired core gas using a gas exchange process, discussed in more detail below.

In embodiments, a microbubble system can provide a suspension of microbubbles for use in a medical application or other applications. For example, the microbubble system can be configured to generate microbubbles on demand for immediate use, for example, by rehydrating, defrosting, and/or changing the core gas of a stored microbubble population. The microbubbles may be generated online (i.e., internal to the system) or at a remote location, such as a central production station located at a treatment site (e.g., at a hospital) or a central manufacturing facility (e.g., manufacturing plant). The microbubble system can be configured to provide a microbubble suspension after a short startup delay (e.g., less than one minute). The microbubbles may be stored external to the microbubble system until ready for use, such as in a sealed container. Alternatively, the microbubbles can be stored internal to the microbubble system, such as in a sealed volume of a fluid circuit or in a sealed container kept onboard. Of course, commercial embodiments may incorporate one or more aspects of the above examples.

Figure 4:
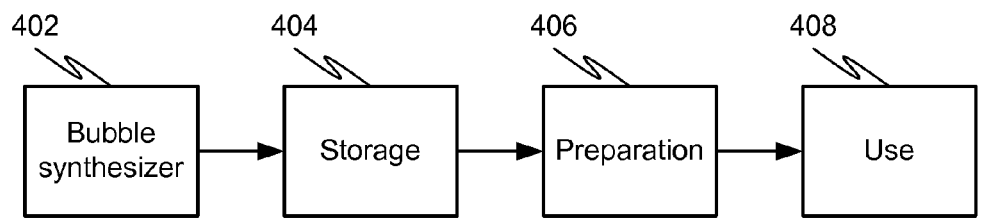
FIG. 4 is a schematic diagram of a microbubble system, according to one or more embodiments of the disclosed subject matter.

Referring now to FIG. 4, a schematic diagram of a microbubble system is shown. A microbubble synthesis system 402 produces gas-filled microbubbles. The microbubbles may be produced by ultrasonically agitating a lipid-gas interface in a reaction volume. The resulting microbubbles have a lipid monolayer surrounding a core composed substantially of the gas. The microbubbles can be subjected to various processes in the synthesis system 402, such as selecting a portion of the microbubbles based on size and/or concentrating the microbubbles to have a desired gas volume percentage.

A storage system 404 can process the microbubbles for storage. For example, the storage system 404 can freeze, or freeze-dry, the microbubbles. The storage system 404 can seal the frozen or freeze-dried microbubbles in a container to keep them ready for use. The storage system 404 can also be configured to maintain a temperature of the container below room temperature, and the microbubbles withdrawn as needed. For example, the container can be a sealed receptacle with a septum.

A preparation system 406 can prepare the stored microbubbles for use. For example, the preparation system 406 can include a precision heating/cooling device for raising the temperature of frozen microbubbles at a controlled rate. The heating/cooling device can be configured to quickly bring the temperature of the microbubbles to room temperature from dry ice temperatures, for example, in less than a minute. The preparation system 406 can also include a gas exchange device to fill the core of the microbubbles with the desired gas, for example, oxygen.

The preparation system 406 can also include infusion preparation components, such as, but not limited to, a mixing device, an air/bubble removing device, and a testing device. The mixing device can be engineered to mildly agitate the microbubble suspension with minimal shear stress to ensure a relatively homogeneous mixture with no microbubble clumps. The air/bubble removing device can be constructed to remove bubbles that exceed a certain size range, e.g., greater than 10 µm. In addition, any undesired air bubbles that may be in the solution due to the storage or processing can be removed. The testing device may test the microbubble suspension prior to use to ensure that microbubbles meet desired criteria, such as size distribution or gas concentration.

The resulting microbubbles can then be used in a desired application. For example, system 408 can include an infusion device configured to infuse the gas-filled microbubbles into a patient. The infusion device can include an infusion or syringe pump for introducing the microbubbles into the vascular system of a patient. In another example, system 408 is an industrial unit for introducing the microbubbles into solution in an industrial process. Of course, other types of systems 408 for a variety of different uses are also possible according to one or more contemplated embodiments.

Figure 5:
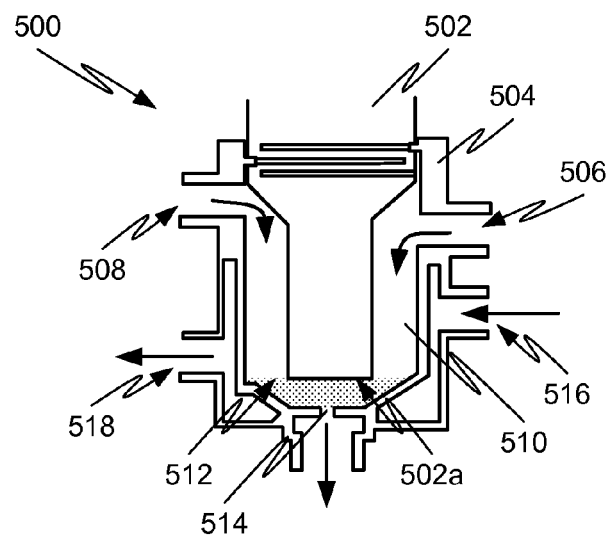
FIG. 5 is a schematic diagram of a microbubble synthesis device, according to one or more embodiments of the disclosed subject matter.

Referring to FIG. 5, a microbubble synthesis device 500 that can be used to ultrasonically generate microbubbles is shown. Synthesis device 500 can provide a substantially air-free environment for microbubble synthesis and collection. The flow chamber 504 of the device 500 has an ultrasonic horn 502 (i.e., sonicator) enclosed therein. A lipid solution injected into inlet 506 of the flow chamber 504 can be combined with a gas injected into inlet 508 of the flow chamber 504. The lipid solution can be delivered to the lower inlet 506 of the two side inlet ports 506, 508 of the flow chamber 504 by, for example, a pump (not shown).

The flow chamber 504 may have a reaction chamber 510 therein with a relatively high cup resulting in a shallow draft. Ultrasonic agitation (e.g., ~20 kHz) of the interface 512 between the lipid solution and the gas in the reaction volume 510 adjacent the tip 502a of horn 502 in the flow chamber 504 results in the production of gas-filled microbubbles. The generated microbubbles can be pulled from the shallow gap between the sonicator tip 502a and a bottom of the reaction chamber 510 via outlet 514, located at the bottom of the reaction chamber 510.

Figure 6:
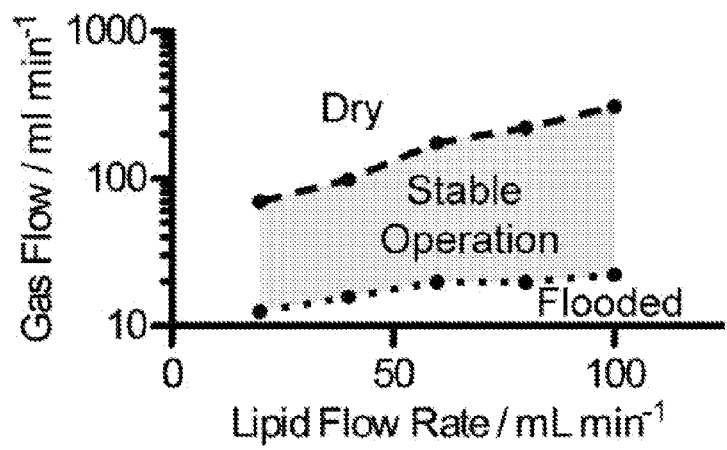
FIG. 6 is a graph illustrating flow chamber operation parameters for various gas and lipid flow rates.

A cooling fluid, such as water, can be circulated through the flow chamber 504 via inlet port 516 and outlet port 518 to moderate the temperature of the reaction volume 510. For example, the cooling fluid can be circulated through an outer portion of the flow chamber 504 at 10° C. using a temperature control bath. The module 500 can handle lipid solution flow rates in excess of 100 ml/min with no detectable change in resulting microbubble properties for a wide range of lipid and gas flow rates, as shown in FIG. 6.

An appropriate lipid mixture for use in producing microbubbles can include 90 mol % of 1,2-dipalmitoyl-sn-glycero-3-phosphocholine (DPPC), 10 mol % of polyethylene glycol stearate (PEG-40S), and phosphate buffered saline (PBS) solution. The DPPC, a saturated sixteen carbon chain phospholipid, can provide for low surface tension at the gas-liquid interface and is a major component of pulmonary surfactant. The stearate end of the PEG can facilitate lipid dispersion and can decrease microbubble coalescence. The buffered saline solution can be used to maintain a constant pH. In addition, the organic compounds of the monolayer mixture can be used for the purpose of its neutral effects when injected into the bloodstream of a patient.

The continuous flow attachment allows the constant exposure of lipid solution and gas to high intensity sonication (e.g., ~20 kHz and 400 W) in a reaction chamber, the volume of which can be controlled. The gap between the sonicator tip and the bottom of the reaction volume is directly related to the power density of the sonicator and thus can be optimized for efficient microbubble production. The sonicator probe 502 can be screwed into the flow chamber 504. The number of turns that the probe 502 is screwed into the flow chamber 504 can determine the volume of the reaction chamber gap.

The operating conditions of the sonicator 502 can be at its highest power intensity (e.g., 400 W), with a lipid flow rate of, for example, 108.7 ml/min, a gas flow rate of 75 ccm, and a ¼ gap turn in the flow chamber. These operating conditions can result in the formation of microbubbles less than 10 μm in size. The microbubble generation device serves to direct the gas, such as oxygen, and the lipid composition into the reaction volume, and specifically into a gap between the sonicator probe tip and the bottom outlet of the flow chamber. For example, oxygen flow can be initially set to approximately 60 mL/min. The lipid solution flow rate can be set to approximately 80 mL/min. When the lipid solution reaches the reactor, the sonicator can be turned on to a maximum power output.

Figure 7:
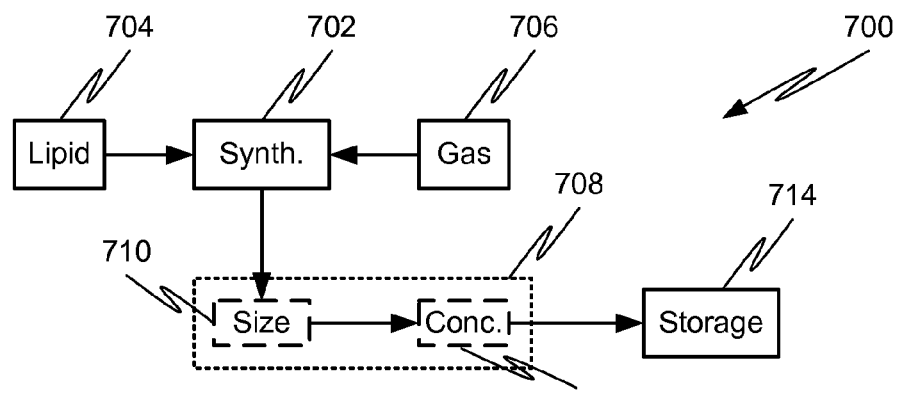
FIG. 7 is a schematic diagram of a microbubble generation system, according to one or more embodiments of the disclosed subject matter.

In embodiments, the microbubbles can be synthesized at a central microbubble generation facility, such as the microbubble generation system 700 shown in FIG. 7. The microbubble generation unit 700 may produce large quantities of microbubbles in desired size ranges. The microbubble generation system 700 can be configured to control the size and/or surface chemistry of fabricated microbubbles, for example, to maximize microbubble yield during fabrication and/or to increase stability during storage. In particular, synthesizer 702, which can include synthesis device 500 of FIG. 5, receives a microbubble shell precursor from source 704 and a gas from gas source 706. The microbubble shell precursor can be a phospholipid-emulsifier mixture as described herein. A phospholipid membrane stabilizer can be added to the lipid solution in source 704 to increase microbubble yield and stability during fabrication in synthesizer 702. Such stabilizers can include, but are not limited to, trehalose. The gas in gas source 706 can be selected to optimize or at least improve microbubble yield and stability. For example, gases which are insoluble in water may increase the stability of the microbubbles and in general make formation of microbubbles easier. Such gases can include, but are not limited to, sulfur hexafluoride and perfluorocarbons.

Microbubbles produced by synthesizer 702 can be conveyed to an optional processing module 708. Processing module 708 can include a size separation module 710 and a concentration module 712. The size separation module 710 can separate the microbubbles according to size so as to isolate the microbubbles of a particular size for a desired application. For example, microbubbles having diameters between 0.5 μm and 10 μm may be isolated for use in medical applications. Other size ranges may also be isolated depending on the requirements of a desired application. The initially isolated microbubble suspension may be relatively dilute, for example, with a concentration of 1% volume gas. For certain application, it may be desirable to increase the microbubble concentration so as to reduce the volume of fluid necessary to deliver a desired gas payload. The isolated microbubbles may thus be concentrated by concentration module 712. The concentration module 712 may increase the concentration to greater than 50% volume gas for use and/or storage.

Microbubbles processed by the processing module 708 may be conveyed to a storage preparation module 714, which prepares the microbubbles for storage. For example, storage preparation module 714 can include a freeze-drying unit, such as unit 800 shown in FIG. 8 and described in more detail below. When freeze-drying the microbubbles for storage, concentration by concentration module may not be necessary. The storage preparation module 714 can include a flash freezer capable of rapidly reducing the temperature of a suspension of microbubbles from approximately room temperature to less than −20° C. (e.g., −78.5° C.). For example, the flash freezer may freeze the microbubble suspension at a cooling rate greater than $10^{4\circ}$ C./min, such as $10^{5\circ}$ C./min. The frozen or freeze-dried microbubbles can be packed in a sealed container for storage and/or transportation.

In an alternative, the storage preparation module 714 can package microbubbles filled with an insoluble or low solubility gas in a sealed container, whereby the insoluble gas may increase the shelf life of the microbubbles. The storage preparation module 714 can also include a gas exchange module to replace the gas in the microbubbles with a desired gas. For example, the gas in the microbubbles may be replaced with a low solubility or insoluble gas for storage purposes. Alternatively, freeze-dried microbubbles may be exposed to a desired gas and stored in a sealed atmosphere thereof in order to fill the microbubble cores with the desired gas. The desired gas can be a gas desired for a particular application or to enhance stability of the microbubbles during storage. For example, in medical applications, the desired gas may be a medically useful gas, such as, but not limited to oxygen and isoflurane. After appropriate storage by unit 714, the microbubbles can be transported to an end user location for use in a desired application.

Figure 8:
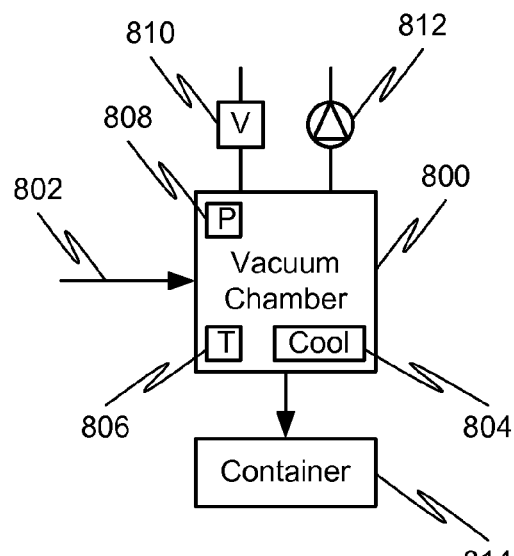
FIG. 8 is a schematic diagram of a microbubble storage unit, according to one or more embodiments of the disclosed subject matter.

To freeze-dry microbubbles for storage, microbubbles can be provided to a temperature-controlled vacuum chamber 800 via inlet 802, as shown in FIG. 8. Vacuum chamber 800 can include a temperature sensor 806 and a cooling device 804. The cooling device 804 can be a flash freezing unit capable of rapidly reducing the temperature of a suspension of microbubbles from approximately room temperature to less than −20° C. For example, the cooling device may freeze the microbubble suspension in the vacuum chamber at a cooling rate greater than $10^{4°}$ C./min, such as $10^{5°}$ C./min. The cooling device 804 may use dry ice, liquid nitrogen, or other low temperature substances to achieve rapid cooling within the vacuum chamber.

The vacuum chamber 800 can also include a pressure sensor 808 for monitoring the pressure within the vacuum chamber during freezing and drying. Valve 810 and pump 812 can be used to regulate the pressure within the vacuum chamber. Once the microbubbles are frozen, pump 812 can draw a vacuum on the chamber 800 such that frozen water sublimes out of the microbubble suspension. The now-dry microbubbles can be provided to a container 814, which may be sealed in a gas atmosphere or under vacuum for transportation and/or storage.

Gas contained in the microbubble cores may also be removed during this process, leaving behind only the phospholipid shell. Pressure transitions from atmospheric pressure to vacuum and from vacuum to atmospheric pressure can be controlled so as to be gradual thereby avoiding unnecessary stress on the microbubble shells, which may damage the shell integrity and reduce the viability of the microbubbles when thawed. The speed of pressure changes may depend on microbubble shell material, microbubble size distribution, the temperature during the pressure variations, the presence or absence of additives or shell stabilizers, and/or the gas used in the microbubble fabrication, among other factors.

Figure 9:
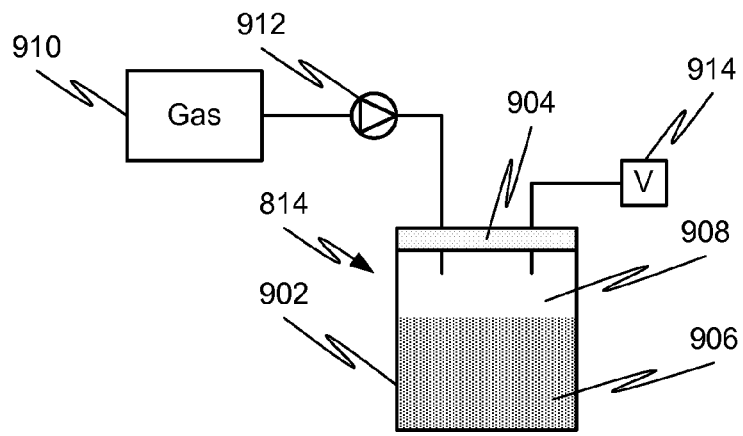
FIG. 9 is a schematic diagram of a gas exchange unit, according to one or more embodiments of the disclosed subject matter.

Container 814 can be stored at a reduced temperature (e.g., $-20°$ C. or less) until ready for use. Since the gas in the microbubbles cores has been removed by the freeze-drying process, the microbubble cores can be back-filled with any desired gas prior to use. Referring to FIG. 9, a setup for filling the cores of freeze-dried microbubbles in a sealed container 814 is shown. For example, container 814 may be a sealed bottle 902 with a septum 904. The interior of the bottle 902 can be accessed by piercing the septum with one or more needles, as shown in FIG. 9. The interior of the bottle 902 is filled with freeze-dried microbubbles 906, leaving a headspace 908 above the microbubbles 906 for injection of a desired gas. Gas from source 910 can be controllably injected via pump 912 and/or a control valve (not shown) into bottle 902 through septum 904, thereby filling headspace 908 with the desired gas. A valve 914 and/or pump (not shown) may also be connected to the interior of bottle 902 to regulate a pressure therein. For example, the pressure may be regulated such that any pressure changes in bottle 902 are gradual.

In addition to pressure changes, abrupt changes in gas composition may affect microbubble integrity. To minimize the impact of gas changes, the composition of gas introduced into microbubbles 906 from gas source 910 may be gradually adjusted over time. For example, when microbubbles 906 and headspace 908 contain a first gas, the composition of gas injected into the headspace from gas source 910 may be progressively changed from substantially a first gas to a mixture of first and second gases to substantially a second gas. Thus, the amount of first gas is gradually decreased as the amount of second gas is gradually increased until only the second gas is present in headspace 908.

Figure 10:
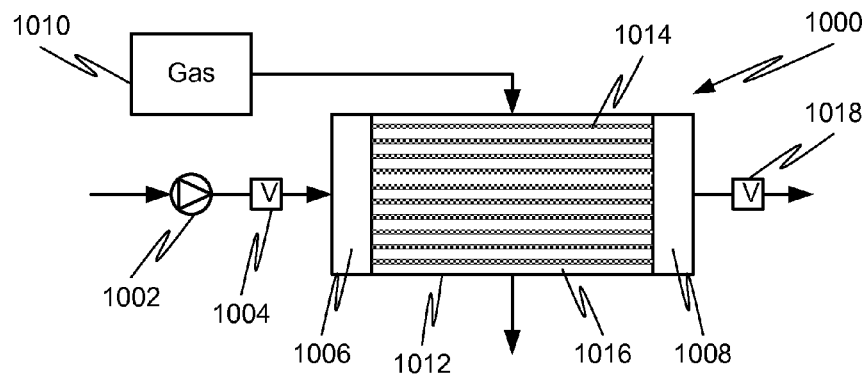
FIG. 10 is a schematic diagram of another gas exchange unit, according to one or more embodiments of the disclosed subject matter.

Other configurations for gas exchange of microbubbles are also possible according to one or more contemplated embodiments. For example, a gas exchange unit 1000 can be used to replace the gas (e.g., a first gas) in the microbubble core with a desired gas (e.g., a second gas), as shown in FIG. 10. Pump 1002 conveys microbubbles into an inlet manifold 1006 of a dialyzer unit 1012. The inlet manifold 1006 can distribute the microbubbles amongst multiple membrane tubules 1014 or hollow fibers within dialyzer unit 1012. For example, microbubbles are flowed in through the inlet manifold 1006 so as to fill the length of the membrane tubules 1014. The membrane of the tubules 1014 separates the microbubbles in the tubules from the interior volume 1016 of the dialyzer unit 1012. Once the tubules are filled with microbubbles, the inlet valve 1004 and the outlet valve 1018 seal the dialyzer 1012 while gas from gas source 1010 is flowed therethrough. Outlet manifold 1008 conveys the microbubbles from the multiple membrane tubules 1014 to an outlet. The interior volume 1016 of the dialyzer unit 1012 between the individual tubules 1014 can be filled with a gas from gas source 1010. Inlet valve 1004 and outlet valve 1018 can be used to seal the dialyzer unit 1012 during gas flow therethrough.

As discussed above, abrupt changes in gas composition may adversely affect microbubble integrity. The composition of gas from source 1010 is thus gradually adjusted over time from substantially the first gas (i.e., the same as the original core gas) to substantially the second gas (i.e., the desired core gas). Once the gas exchange is complete, the outlet valve 1018 may be opened and the microbubbles conveyed from the dialyzer 1012. The dialyzer 1012 can then be refilled so as to process a second batch of microbubbles.

Figure 11:
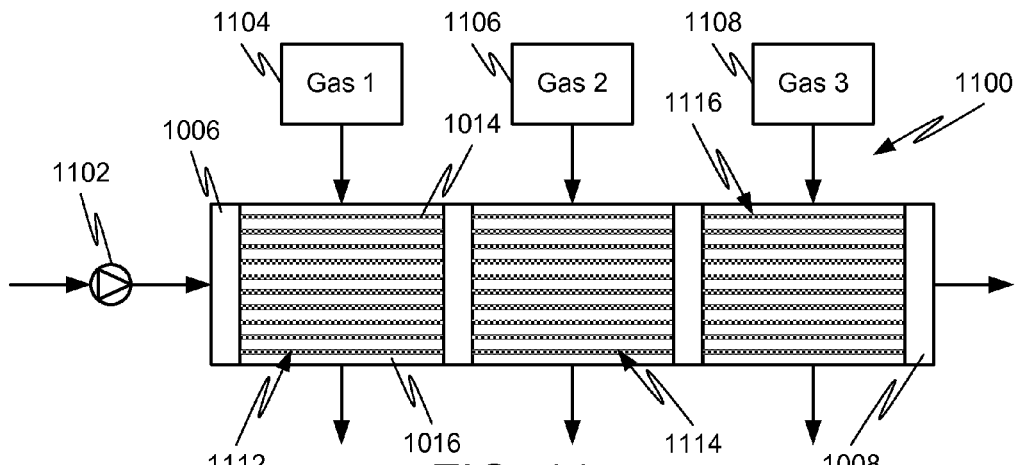
FIG. 11 is a schematic diagram of a third gas exchange unit, according to one or more embodiments of the disclosed subject matter.
Figure 12:
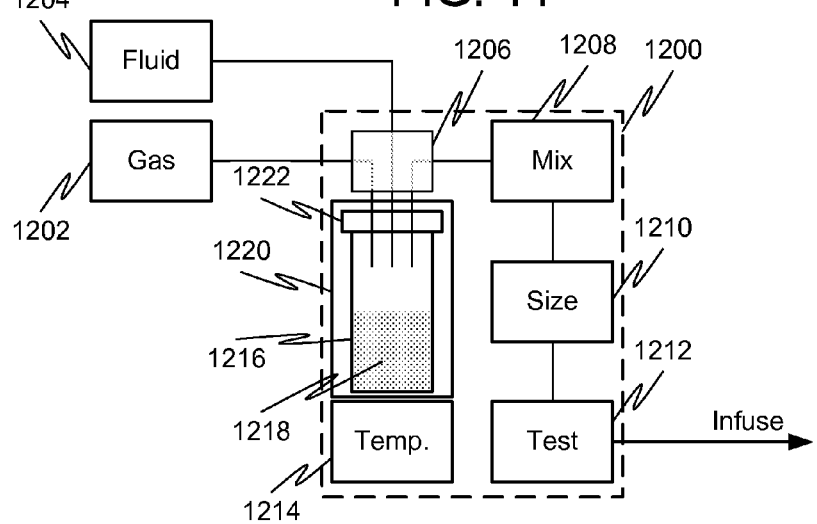
FIG. 12 is a schematic diagram of a microbubble infusion unit, according to one or more embodiments of the disclosed subject matter.

Rather than performing gas exchange on a batch of microbubbles at a time, microbubbles may be continuously processed using gas exchange unit 1100, as shown in FIG. 11. Multiple dialyzers can be serially disposed such that the microbubbles flowing therethrough are exposed to a progressively varying composition of gases. For example, a first dialyzer 1112 can be used to replace the gas (e.g., a first gas) in the microbubble core with a first composition from source 1104. The first composition may be a blend of the first gas and the desired gas (e.g., a second gas), with the first gas comprising the greater portion thereof. The second dialyzer 1114 can be used to replace the gas in the microbubble core with a second composition from source 1106. The second composition may be a blend of the first gas and the second gas, with the second gas comprising the greater portion thereof. The third dialyzer 1116 can be used to replace the gas in the microbubble core with a third composition from source 1108. The third composition may be substantially composed of the second gas.

Replacement of the gas in the core of the microbubbles may occur before or after freeze-drying, for example, after the microbubbles have been rehydrated in preparation for use. In embodiments, the freeze-dried microbubbles themselves may be subjected to gas replacement using the dialyzers of FIGS. 10-11. It is to be noted that other configurations for membrane-based gas exchange are also possible according to one or more contemplated embodiments. For example, instead of tubular membranes, a planar membrane can be used to separate a microbubble solution from a desired gas flowing on an opposite side of the membrane. The desired gas can diffuse across the membrane into the cores of the microbubbles while any undesired gas in the microbubble suspension may diffuse into the gas flow on the opposite side. It is also possible to operate the membrane-based gas exchange devices using a gas-saturated fluid flow on one side of the membrane while the microbubble solution is on the other side of the membrane.

Gas replacement via a membrane may be done in stages to replace the gas progressively. For example, a low ratio of first to second gas may be passed through a first dialytic transfer, followed by a higher ratio, progressively and/or in stages, until only the second gas is passed through the dialyzer. In this way the exchange of gases can be performed in a manner that may be less disruptive to the microbubbles. Alternatively, or in addition, the flow of gas and microbubble suspension may be provided in a counter-flow configuration such that the second gas saturation at the inlet is high but low at the outlet, the gas inlet coinciding with the microbubble outlet such that at all points along the membrane the second gas saturation differs by a selected degree between the gas side and the microbubble suspension side.

After storage, the microbubbles can be prepared for a particular use by reversing any particular storage preparations. In the case of freeze-drying, the microbubbles can be refilled with a particular gas and rehydrated. In the case of freezing, the microbubbles can be quickly heated to room temperature. In the case of using an insoluble gas for storage, appropriate gas exchange can prepare the microbubble core for the desired application.

In embodiments, an infusion unit 1200 can be used to prepare a freeze-dried sample of microbubbles for infusion, for example, into a patient. The infusion unit 1200 may be configured as, for example, a bed-side unit to receive a stored quantity of microbubbles and to quickly prepare the microbubble suspension for immediate infusion. A vial 1216 of freeze-dried microbubbles 1218 sealed by septum 1222 can be provided to a receptacle 1220 of infusion unit 1200 from an internal or separate storage compartment, such as a refrigerator. An actuator 1206 with one or more needles can puncture septum 1222 to provide fluidic access to the interior of vial 1216.

A temperature control module 1214 can provide appropriate temperature control of the contents of vial 1216. Moreover, temperature control module 1214 can be configured to quickly raise the temperature of the vial to room temperature. Temperature control module 1214 may also be configured to maintain the temperature of the vial below room temperature during particular portions of the process, such as during gas exchange. A controller (not shown) may automatically control the operation and timing of the various modules and processes of infusion unit 1200.

Gas from gas source 1202 may be flowed into the vial 1216 to fill the head space thereof and to refill the core (similar to the process described above with respect to FIG. 9). For example, the gas from source 1202 may be a medically useful gas, such as oxygen or isoflurane. Once the cores of the microbubbles are filled with gas, the freeze-dried microbubbles can be rehydrated by the addition of fluid from fluid source 1204. For example, the fluid from fluid source 1204 may be a medically useful fluid, such as water or PBS. Fluid from fluid source 1204 may be added so as to minimize potential damage to the microbubble structure, such as by directing fluid inlet flow and controlling inlet flow rates to reduce direct impact on the microbubbles. Additives or stabilizers may also be added before or during the addition of fluid to improve microbubble stability during rehydration. For example, trehalose may be added to the microbubbles to increase the stability thereof. Because the mass of the microbubbles is relatively small, the addition of the fluid from fluid source 1204 may serve to quickly increase the temperature of the microbubbles to room temperature without any separate heat input from temperature control module 1214.

The microbubble suspension from the vial 1216 can be conveyed to mixing unit 1208, which mixes the microbubble suspension to promote homogeneity and remove clumps. The mixing can gently agitate the suspension while avoiding damage to the lipid monolayer shells of the microbubbles. For example, the microbubbles can be conveyed through dedicated fluidic components designed to gently agitate and mix the microbubbles while minimizing shear stress thereon. For example, the microbubbles may be flowed through a venturi or cuvette. In another example, the microbubbles may be passed through a sieve or grating designed to break up clumps as well as to prevent the passage of microbubbles exceeding a given size. In another example, the microbubble suspension may be agitated via stirring by a stirring rod disposed in the suspension. Other mechanisms for mixing the microbubble suspension are also possible according to one or more contemplated embodiments.

Size sorting unit 1210 can process the microbubble suspension to remove any bubbles that may be outside of a desired size range. For example, for certain medical applications, microbubbles having diameters within a range of 0.5 µm to 10 µm may be useful. While the stored microbubbles may have diameters within this range, storage and processing may result in the coalescence and/or growth of some bubbles that exceed this size range as well as the formation of air or other gas bubbles. The size sorting unit 1210 thus removes these bubbles such that the resulting microbubble suspension again satisfies the desired size range. Sorting can be achieved by various methods, such as, but not limited to, centrifugation, differential flotation, and/or filtering.

A testing module 1212 can confirm that the microbubble suspension meets certain criteria for use. For example, test module 1212 can inspect the microbubble suspension for compliance with a desired microbubble size distribution, a desired gas concentration, and/or lipid material integrity. Size distribution can be measured using optical techniques, such as laser light obscuration and scattering. Gas concentration can also be determined using optical techniques, such as light obscuration, microscopy, ultrasonic imaging, and/or other techniques. Lipid material integrity can also be evaluated using chromatography or optical chromatography. Digital images or other data representing microbubble characteristics can be processed automatically using machine recognition techniques to identify and correct undesired characteristics in an online system.

The infusion unit 1200 can be configured to quickly produce a microbubble suspension for use with minimal notice. For example, the infusion unit can be configured to produce microbubbles from a stored vial of freeze-dried microbubbles in less than 5 minutes, for example, less than 2 minutes. Infusion unit 1200 may perform gas exchange and rehydration of the freeze-dried bubbles at a patient's bedside for immediate infusion. Alternatively, gas may be added to freeze-dried microbubbles prior to the infusion unit 1200, such as at the factory or in a separate station, such as at an onsite storage facility. For example, a medical facility may receive a shipment of microbubbles from the factory with a storage gas or no gas contained therein. The storage gas may be relatively insoluble or have a low solubility to enhance the stability of the microbubbles. Once received onsite, the gas may be exchanged to fill the microbubble core with a medically useful gas, such as oxygen or isoflurane. The medical facility may thus maintain a large quantity of oxygen filled microbubbles on site in freeze dried form and ready for immediate use by machine 1200 without any gas exchange. In such a configuration, the gas exchange aspects of machine 1200 may be omitted.

Figure 13:
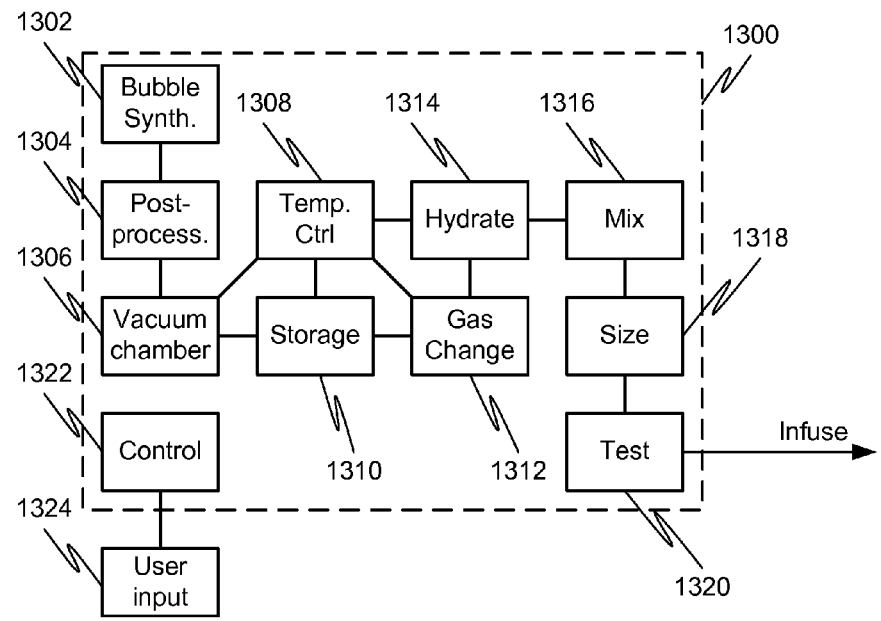
FIG. 13 is a schematic diagram of an integrated microbubble system employing freeze-drying, according to one or more embodiments of the disclosed subject matter.

In embodiments, generation, storage, and preparation of microbubbles for infusion can be integrated into a single system, such as microbubble system 1300. Referring to FIG. 13, an integrated microbubble system 1300 using freeze-drying for on-board microbubble storage is shown. The microbubble system 1300 includes a controller 1322, which controls operation of the system 1300 and the various sub-units 1302-1320. A user interface 1324 allows a user to control operation of the microbubble system. For example, a user can set a desired microbubble size range, a desired gas concentration, a desired infusion rate, and/or other system parameters via user interface 1324.

The integrated microbubble system 1300 can include a microbubble synthesis unit 1302, such as the microbubble synthesis device of FIG. 5, which can generate a population of microbubbles using a first gas. The first gas may be the same as an eventually desired core gas, or it may be different. The generated microbubbles may undergo post-processing in unit 1304. For example, post-processing unit 1304 may select a portion of the microbubbles that meet a desired size range. Unused microbubbles may be recycled to the microbubble synthesis unit 1302 or discarded. The selected microbubbles can be conveyed to a vacuum chamber 1306, wherein the microbubbles are freeze-dried. Temperature control unit 1308 can control the temperature of the freeze-drying process in vacuum chamber 1306. The freeze-dried microbubbles can be stored in on-board storage 1310. Temperature control unit 1308 can also maintain the temperature of the on-board storage, for example, below −20° C. Alternatively, temperature control unit 1308 can maintain the temperature of the on-board storage for the freeze-dried microbubbles substantially at room temperature.

Prior to use, the freeze-dried microbubbles can be subject to gas exchange in gas exchange unit 1312. The gas exchange unit 1312 may backfill the microbubbles cores with a desired second gas. Note that the desired second gas may be the same as or different from the first gas used to produce the microbubbles in microbubble synthesis unit 1302. Temperature control unit 1308 can also maintain the temperature of the gas exchange unit. The freeze-dried microbubbles can be rehydrated and suspended via hydration unit 1314, which adds water or other solution to the microbubbles in a controlled manner. Temperature control unit 1308 can control the temperature during the hydration process such that the microbubbles are brought to room temperature quickly. Mixing unit 1316 can gently agitate the microbubbles to provide a relatively homogenous dispersion. Size sorting unit 1318 can process the microbubble suspension to remove any bubbles that may be outside of a desired size range, while testing module 1320 may confirm that the microbubble suspension is suitable for infusion.

Figure 14:
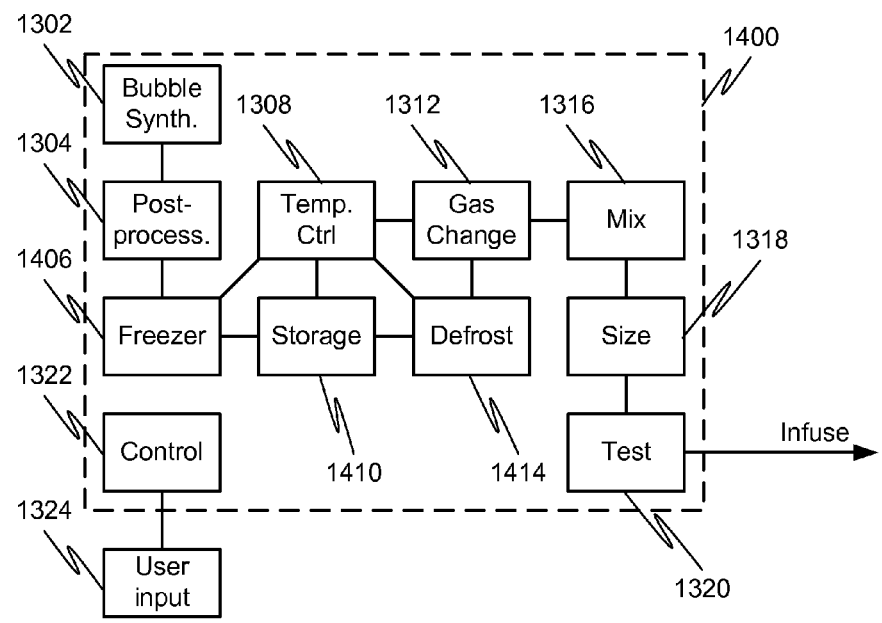
FIG. 14 is a schematic diagram of an integrated microbubble system employing freezing, according to one or more embodiments of the disclosed subject matter.

Referring to FIG. 14, an integrated microbubble system 1400 using freezing for on-board microbubble storage is shown. System 1400 is similar to system 1300, but vacuum chamber 1306 is replaced with flash freezing unit 1406. Flash freezing unit 1406 is configured to rapidly freeze the microbubble suspension after processing by unit 1304. Temperature control unit 1308 can control the temperature of the flash freezing unit 1406. The frozen microbubble suspension can be stored in on-board storage 1410. Temperature control unit 1308 can also maintain the temperature of the on-board storage 1410 at a reduced temperature, for example, below −20° C. A defrosting unit 1414 can take the frozen microbubble suspension from on-board storage 1410 and rapidly bring it to room temperature in preparation for infusion. Prior to use, the frozen microbubbles can be subject to gas exchange in gas exchange unit 1312. The gas exchange unit 1312 may backfill the microbubbles cores with a desired second gas. Note that the gas exchange can occur prior to freezing by freezer 1406 or after thawing by defrosting unit 1414.

Figure 15:
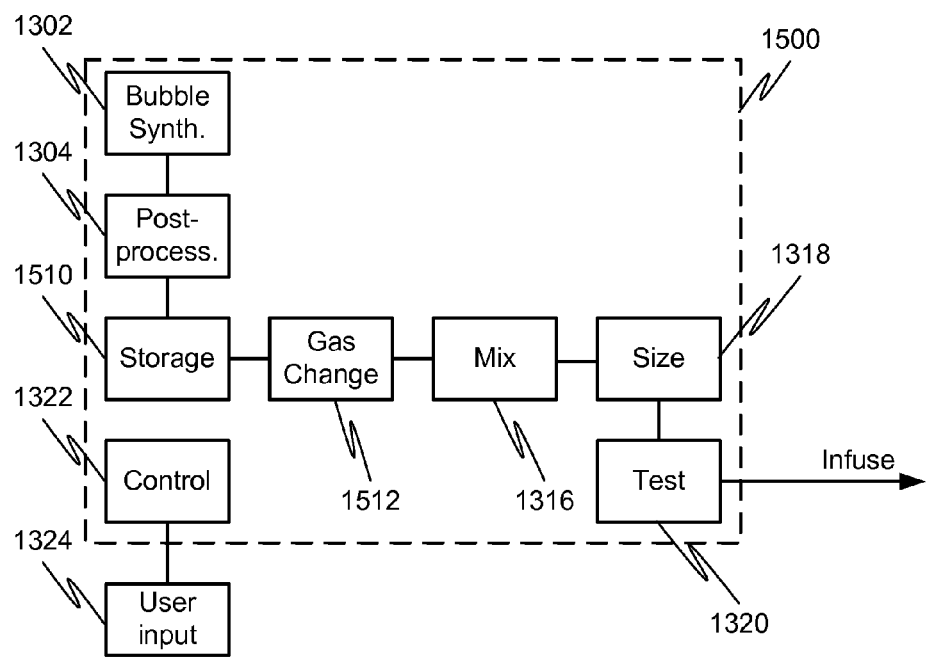
FIG. 15 is a schematic diagram of another integrated microbubble system, according to one or more embodiments of the disclosed subject matter.

Referring to FIG. 15, an integrated microbubble system 1500 using an insoluble gas for on-board microbubble storage is shown. System 1500 is similar to system 1300, but the vacuum chamber, temperature controller, and hydration unit are omitted. The microbubble synthesis unit 1302 can generate a population of microbubbles using a first gas, which is insoluble or has a low solubility. Because of the increased stability of the first-gas-filled microbubbles, the microbubble suspension can be directly stored on-board in storage 1510. Prior to use, the stored microbubbles can be subjected to gas exchange in gas exchange unit 1512. The gas exchange unit 1512 may backfill the microbubble cores with the desired second gas. Note that the desired second gas can be different from the first gas used to produce the microbubbles in synthesis unit 1302. For example, the desired second gas may be a medically useful gas, such as oxygen or isoflurane.

In embodiments, a central processing facility can use an insoluble or low solubility gas for fabrication and storage of the microbubbles. Since the first gas is relatively insoluble, the produced microbubbles can have enhanced stability as compared with microbubbles filled with a more soluble core gas. However, the more soluble core gas may be more useful for a desired application. For example, the desired core gas may be a medically useful gas, such as oxygen or isoflurane. Prior to use, the microbubbles may undergo gas exchange to replace the gas in the microbubbles with the desired second gas. This gas exchange can occur at the central processing facility. In embodiments, the gas exchange may be postponed as long as possible to take advantage of the improved storage afforded by using the first gas as the core gas. Such gas exchange may take place at the point of use, for example, just prior to infusion at a patient treatment location.

Embodiments described herein can be configured as mobile systems or devices, such that they can be moved, for example, from room to room in a hospital. Embodiments can be deployed in mobile medical units, such an ambulance or medivac helicopter, for use by emergency personnel. Alternatively, the embodiments can be configured as a portable device that emergency responders can carry to a treatment site. In yet another alternative, embodiments can be configured as substantially fixed units with appropriate fluid conveyances and/or storage vessels for transporting generated microbubbles to a target or treatment location. In still another alternative, embodiments can be fixed at a particular location, such as a floor or wing of a medical treatment facility, to prepare microbubbles for use at that location.

Although particular configurations have been discussed herein, other configurations can also be employed. Furthermore, the foregoing descriptions apply, in some cases, to examples generated in a laboratory, but these examples can be extended to production techniques. For example, where quantities and techniques apply to the laboratory examples, they should not be understood as limiting. In addition, although certain materials and gases for the microbubbles have been described herein, other materials and gases (elemental or compositions) are also possible according to one or more contemplated embodiments.

Note that the term "suspension" has been used broadly herein to refer to microbubbles in any form, whether dispersed in a solution matrix, compacted in cake form that consists largely of microbubble shells, or even in a dried form.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided, in accordance with the present disclosure, systems, methods and devices for microbubbles. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A microbubble method comprising:
generating a plurality of microbubbles by ultrasonically agitating an interface between a lipid solution and a first gas in a reaction volume, each generated microbubble having a lipid monolayer shell surrounding a core of the first gas;
freezing the generated plurality of microbubbles so as to remove water and the first gas therefrom, leaving behind freeze-dried lipid monolayer shells;
sealing the freeze-dried lipid monolayer shells in a storage container under vacuum;
storing the freeze-dried lipid monolayer shells under vacuum in the sealed storage container for at least a first time period; and
after the first time period, exposing the freeze-dried lipid monolayer shells to an atmosphere of a second gas such that the core of each lipid monolayer shell is filled with the second gas,
wherein the second gas is different from the first gas.

2. The microbubble method of claim 1, wherein the first time period is one week.

3. The microbubble method of claim 1, wherein the storing the freeze-dried lipid monolayer shells comprises maintaining a temperature in the sealed storage container less than 0° C.

4. The microbubble method of claim 1, wherein said first gas includes one of a perfluorocarbon and sulfur hexafluoride, and said second gas includes one of oxygen and isoflurane.

5. The microbubble method of claim 1, wherein the freezing the generated plurality of microbubbles comprises cooling the microbubbles to a temperature less than −20° C.

6. The microbubble method of claim 1, further comprising:
after the exposing to the atmosphere of the second gas, dispersing the second-gas-filled microbubbles in suspension;
processing the second-gas-filled microbubble suspension to mix and remove microbubbles having a diameter greater than 10 μm therefrom; and
infusing the processed second-gas-filled microbubble suspension into a patient.

7. The microbubble method of claim 1, wherein the exposing to the atmosphere of the second gas comprises flowing the second gas on one side of a membrane while the lipid monolayer shells are on an opposite side of the membrane.

8. The microbubble method of claim 1, further comprising, prior to the exposing to the atmosphere of the second gas, transporting the sealed storage container from a first location, where the sealing in the storage container is performed, to a second location different from the first location.

9. A microbubble method comprising:
flowing a first gas and a lipid solution into a reaction volume;
actuating an ultrasonic agitator disposed at an interface between the lipid solution and the first gas in the reaction volume to generate a plurality of microbubbles, each microbubble having a monolayer shell formed by lipids of the lipid solution, the lipid monolayer shell having an internal volume of the first gas;
freezing the generated microbubbles so as to remove water and the first gas therefrom, leaving behind freeze-dried lipid monolayer shells;
sealing the freeze-dried lipid monolayer shells in a container under vacuum;
storing the sealed container for at least a first time period, the sealed container maintaining the freeze-dried lipid monolayer shells under vacuum during said storing; and
after the first time period, filling the internal volume of the lipid monolayer shells with a second gas different from the first gas.

10. The microbubble method of claim 9, wherein the first time period is one week.

11. The microbubble method of claim 9, wherein the storing the sealed container comprises maintaining a temperature of the freeze-dried microbubbles less than 0° C.

12. The microbubble method of claim 9, wherein said first gas includes one of a perfluorocarbon and sulfur hexafluoride, and said second gas includes one of oxygen and isoflurane.

13. The microbubble method of claim 9, wherein the freezing the generated microbubbles comprises cooling the microbubbles to a temperature less than −20° C.

14. The microbubble method of claim 9, further comprising:
after the filling with the second gas, dispersing the second-gas-filled microbubbles in suspension;
processing the second-gas-filled microbubble suspension to mix and remove microbubbles having a diameter greater than 10 μm therefrom; and
infusing the processed second-gas-filled microbubble suspension into a patient.

15. The microbubble method of claim 14, further comprising, prior to the filling with the second gas, transporting the sealed container from a first location, where the sealing in the container is performed, to a second location where the infusing into the patient is performed.

16. The microbubble method of claim 9, wherein the filling with the second gas comprises flowing the second gas on one side of a membrane while the lipid monolayer shells are on an opposite side of the membrane.

17. A microbubble method comprising:
providing a plurality of microbubbles, each microbubble having a monolayer shell formed by lipids of the lipid solution, the lipid monolayer shell having a core of the first gas;
freezing the plurality of microbubbles so as to remove water and the first gas therefrom, thereby providing freeze-dried lipid monolayer shells;
sealing the freeze-dried lipid monolayer shells in a container under vacuum; storing the sealed container holding the freeze-dried lipid monolayer shells under vacuum for at least one week.

18. The microbubble method of claim 17, further comprising, after the storing the sealed container, filling the core of each lipid monolayer shell with at least a second gas different from the first gas.

19. The microbubble method of claim 18, wherein the freezing the plurality of microbubbles is performed using a freeze-drying unit and the filling with at least the second gas is performed using a gas exchange unit different from the freeze-drying unit.

20. The microbubble method of claim 18, further comprising:
prior to the filling with at least the second gas, transporting the sealed container from a first location, where the sealing in the container is performed, to a second location;
after the filling with at least the second gas, dispersing the microbubbles in suspension;

processing the microbubble suspension to mix and remove microbubbles having a diameter greater than 10 μm therefrom; and at the second location, infusing the processed microbubble suspension into a patient.

\* \* \* \* \*